United States Patent [19]

Tasto et al.

[11] 4,263,920
[45] Apr. 28, 1981

[54] METHOD OF AND DEVICE FOR DETERMINING INTERNAL BODY STRUCTURE

[76] Inventors: Manfred Tasto, Jahnstrasse 26, 2359 Henstedt-Ulzburg; Hermann Schomberg, König-Heinrich-Weg 127D, 2000 Hamburg 61, both of Fed. Rep. of Germany

[21] Appl. No.: 24,273

[22] Filed: Mar. 26, 1979

[30] Foreign Application Priority Data

Mar. 25, 1978 [DE]  Fed. Rep. of Germany ....... 2813068

[51] Int. Cl.$^3$ ................................................ A61B 5/04
[52] U.S. Cl. ...................................... 128/734; 324/62
[58] Field of Search ............... 128/630, 653, 713, 734; 324/57 R, 62 R, 65 R; 364/481–482

[56] References Cited

U.S. PATENT DOCUMENTS

| | | | |
|---|---|---|---|
| 3,452,743 | 7/1969 | Rieke | 128/713 |
| 3,784,908 | 1/1974 | Anderson | 128/734 |
| 3,971,366 | 7/1976 | Motoyama | 128/734 |

FOREIGN PATENT DOCUMENTS

157051  1/1962  U.S.S.R. .................................. 128/670

OTHER PUBLICATIONS

Swanson, D. K., "Measurement Errors and Origin of Electrical Impedance Changes in the Limit," Thesis Subm. to Grad. Sch., Univ. of Wisc–Madison, May 17, 1976, Ch. IX pp. 180–195.
Henderson, R. P. et al., "An Impedance Camera for Spatially Specific Measurements of the Thorax," IEEE Biomed. Engr. Trans., vol. BME25, No. 3, May 1978, pp. 250–254.

Primary Examiner—Robert W. Michell
Assistant Examiner—Francis J. Jaworski
Attorney, Agent, or Firm—Thomas A. Briody; Robert T. Mayer; Jack E. Haken

[57] ABSTRACT

Determining the internal structure of a body, for example, a human body, by means of an electric field which extends between individual electrodes of an electrode array which at least partly surrounds the body. Each time the value of the currents flowing through the individual electrodes is measured. From the currents electrical resistance values in individual tubes of flux generated between the electrodes are measured. By exposure of the body successively to electric fields which each have a different direction and by measurement of the resistance values then occurring, the specific resistance in individual elements of a matrix which is imagined to be stationary with respect to the body can be determined. From the given distribution of the specific resistance in the elements of the matrix, resistance values are calculated in all tubes of flux successively at least once for each field direction. For determination of a correction for the specific resistance in the elements of the matrix, the calculated resistance values are compared with the measured resistance values. The magnitude of the difference determines the magnitude of the correction.

15 Claims, 19 Drawing Figures

METHOD OF AND DEVICE FOR DETERMINING INTERNAL BODY STRUCTURE

The invention relates to a method of determining the internal structure of a body which is exposed to an electric field which extends between individual electrodes of an electrode array which at least partly surrounds the body, currents which flow between the individual electrodes being measured and electrical resistance values in the individual tubes of flux generated between the electrodes being determined from said currents.

The invention furthermore relates to a device for performing a method in accordance with the invention.

A method of this kind is known from "Proceedings 29th ACEMB", Boston, Mass., 1976. According to this known method, the body to be examined, for example, a human thorax, is arranged between a first and an equally large second electrode, the second electrode being subdivided into an electrode field which consists of rows and columns and which is assembled from individual measuring electrodes. An electric alternating voltage is applied between the first electrode and the individual measuring electrodes, so that an electric field which extends through the body is formed therebetween. The current flowing through the measuring electrodes is then a measure for an electric resistance value of the body in a tube of flux which is situated between a measuring electrode and the first electrode and whose dimensions are determined by the measuring electrode. The body can thus be represented as a matrix of resistance values consisting of rows and columns, so that an image is obtained in a plane perpendicular to the field direction, each row or each column consisting of one-dimensional image data. The data in the second dimension of the body, extending in the direction of a tube of flux, is then lost.

However, it has been found that determination of a two-dimensional or three-dimensional structure distribution in a body is desirable. The invention has for its object to provide a method whereby a two-dimensional or three-dimensional structure distribution of a body exposed to an electric field can be determined.

To this end, the method in accordance with the invention is characterized in that the body is successively exposed to differently directed electric fields, for each field direction electric currents being measured in the individual tubes of flux which occur between the electrodes and which differ for each field direction, after which the measured currents are used to determine resistance values wherefrom specific resistance values in individual elements of a matrix which is imagined in the body exposed to the successive fields, for each field direction the tubes of flux and equipotential lines associated with this field direction being determined at least once from a given distribution of specific resistance values over the elements, after which for each tube of flux an associated resistance value is determined from the given specific resistance distribution, after which each calculated resistance value a correction resistance distribution for the tube of flux is calculated by determination of the difference with respect to the resistance value measured in the associated tube of flux, a correction for the specific resistance value for each element being calculated from said correction resistance distributions by interpolation.

This method enables determination of a two-dimensional or three-dimensional structure distribution, for example, a distribution of the specific resistance, in a body exposed to an electric field, for example, a resistance distribution of a human thorax or of an arm. To this end, the specific resistance of the body is determined in individual elements of a matrix which is imagined in the body, it being possible, for example, to convert the individual values of the specific resistance into corresponding grey values for the display of a resistance distribution in a plane on a monitor.

The given resistance distribution to be used for the method is either a resistance distribution determined from a preceeding calculation or a distribution selected on the basis of an anatomical atlas, so that the resistance distribution to be ultimately calculated is closely approximated and the corrections following from the calculations are not excessively large. It has been found that this is advantageous, because the number of iterations to be executed per field direction is thus limited.

In many cases it is not necessary to determine a three-dimensional structure distribution of a body, so that it suffices to produce a specific resistance distribution in a plane of the body exposed to the field. The amount of work and hence the time required for determining the distribution of the specific resistance for the examination of the body is thus reduced.

One version of the method in accordance with the invention is characterized in that the electrode array is rotated around an axis which extends through the body, said axis being constantly directed transversely of the electric field generated between the electrodes, a position thereof remaining unchanged with respect to each electrode.

It is thus achieved that during rotation of the electrode array around the body, the electric field always extends in the same plane and that the electrode array always occupies a prescribed position, which is necessary for the reconstruction of an internal structure of a body being examined from the measurement. The electrical contact between the electrodes and the body can be realized via an electrolyte which surrounds the body to be examined and whose specified resistance is known and does not excessively deviate from the specific resistance of the body to be examined. If the body to be examined is, for example, part of a human body, the electrolyte may be water.

The direction of the field can alternatively be reversed by pole reversal of all electrodes of the electrode array. It is thus achieved that the electrode device need no longer be rotated fully around the body to be examined. If the sense of rotation of the field is reversed for each direction of the electric field, rotation of the electrode array through an angle of, for example, 180° actually suffices for the execution of resistance measurements in all directions within an angle of 360°. The time required for measuring the resistance values along the individual tubes of flux can thus be substantially cut in half.

A further version of a method in accordance with the invention is characterized in that the successively differently directed fields are generated by pole reversal of individual electrodes of the electrode array, the position of the electrode array remaining unchanged with respect to the body to be examined. In order to enable the electrical field to assume any direction in the plane of the body to be examined, the body is fully enclosed by individual electrodes which are situated in the plane, the polarity of said electrodes being changed each time so that a rotation is realized of the field direction between the individual electrodes which are stationary with respect to the body. In order to avoid an excessive potential difference from arising between neighbouring individual electrodes of different polarity, the voltage present on the individual electrodes can be reduced in the direction of the polarity difference from electrode to electrode. Because rotation of the electrode array with respect to the body is avoided, the time required for measuring the resistance values in the individual tubes of flux can be minimized.

According to a further version of a method in accordance with the invention, the electrode are connected to an alternating voltage in order to generate the field between individual electrodes of the electrode array. As a result, polarization of a body present between the individual electrodes is avoided.

The invention also relates to a device for performing the method in accordance with the invention, comprising a power supply source and an electrode array for generating an electric field, at least part of the electrodes of said electrode array being connected to a measuring system for measuring currents flowing through the individual electrodes, said currents being a measure for the resistance values of tubes of flux generated between electrodes of different polarity, a memory for the storage of values obtained and a display device for the display of values obtained, characterized in that the device comprises means for generating successive electric fields in different directions by means of the electrode array, all fields being directed substantially transversely of an axis extending through the body, the measuring system being suitable for measuring the currents flowing through the individual electrodes at the different field directions, said device furthermore comprising a first storage section for the storage of values which are a measure for the direction of the successive fields and for storing the resistance values to be derived from the currents measured which are associated with the direction of the field generating the currents, a second storage section for the storage of specific resistance values, each of which is associated with one element of a matrix of elements, a third storage section for the storage of further data, and a central processor unit:

for determining from the specific resistance values and for a given field direction, field and equipotential lines which subdivide a space defined by the matrix into meshes, values which determine dimensions of the meshs being stored in the third storage section, for determining, by interpolation, a specific resistance in each mesh from the specific resistance values in the elements on the basis of given coordinates of each mesh, said specific resistance being stored in the third storage section, for calculating a resistance value between two field lines by summation of mesh resistance values which are directly proportional to the specific resistance and the length and inversely proportional to the width of the associated mesh, for determining, from the difference between the resistance value measured and calculated for the given field direction, a correction resistance distribution per mesh which is directly proportional to said difference and to the length and inversely proportional to the width of the mesh, said correction resistance distribution being stored in the third storage section;

for determining, by interpolation, from the correction resistance distribution a correction for the specific resistance values in each element, for adding the correction to the associated specific resistance value, a sum thus obtained being stored in the second storage section.

The invention will be described in detail hereinafter, with reference to the accompanying diagrammatic drawing.

Figure 1:
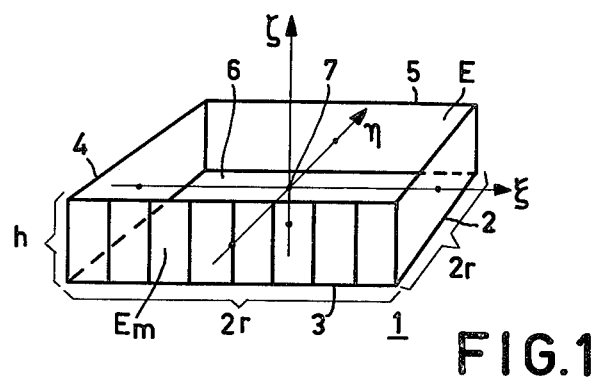
FIG. 1 shows a box-like electrode array for the description of the method.
Figure 5:
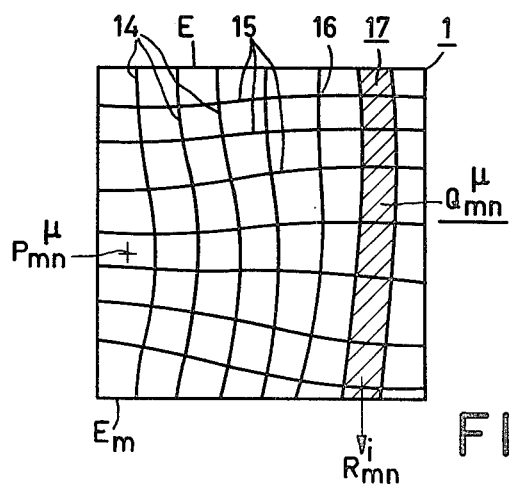
Figure 6:
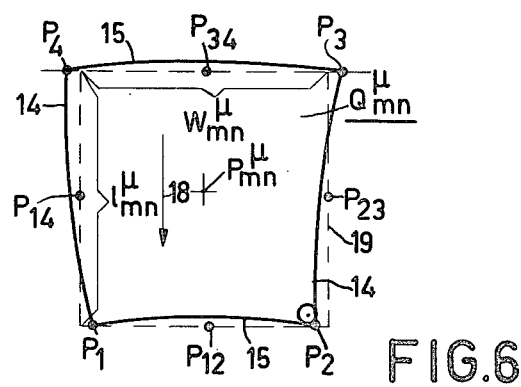
Figure 7:
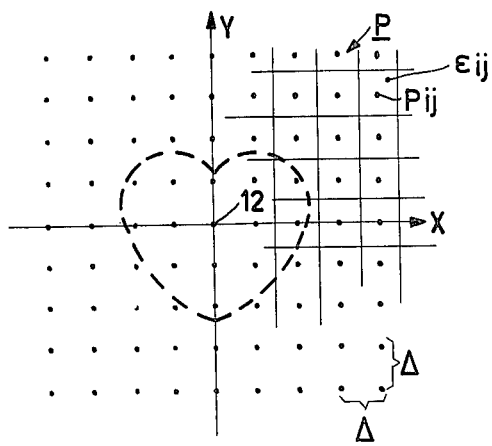
Figure 8:
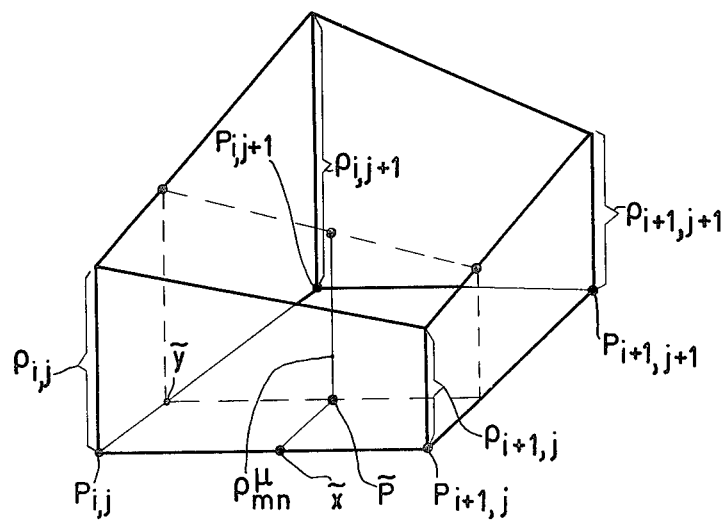
Figure 9:
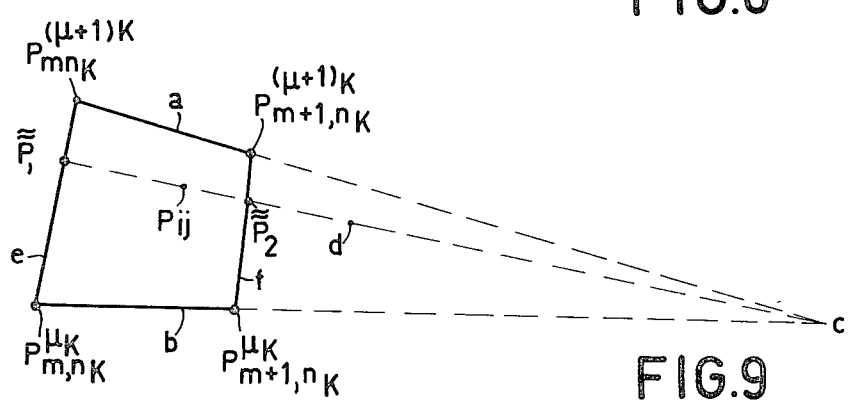
Figure 10:
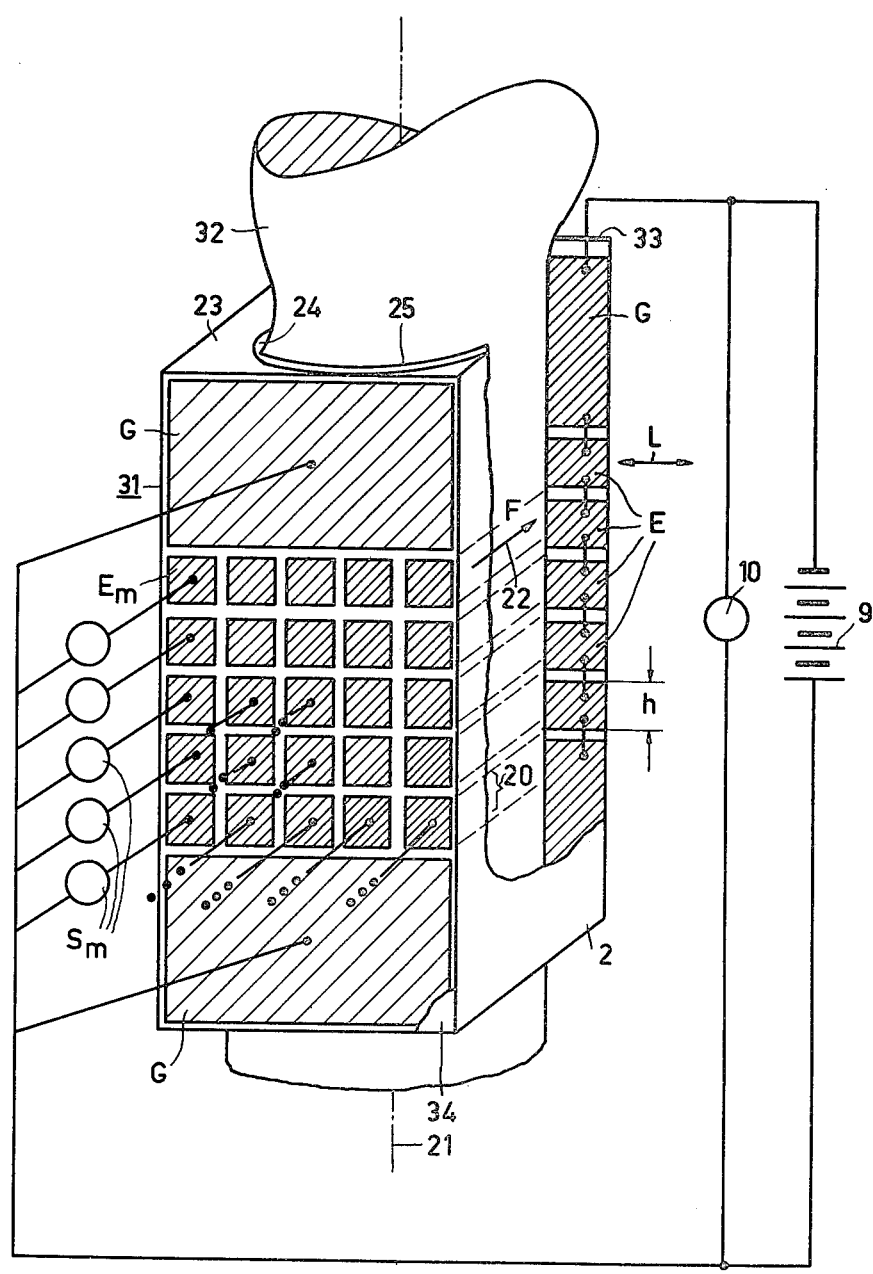
Figure 11A:
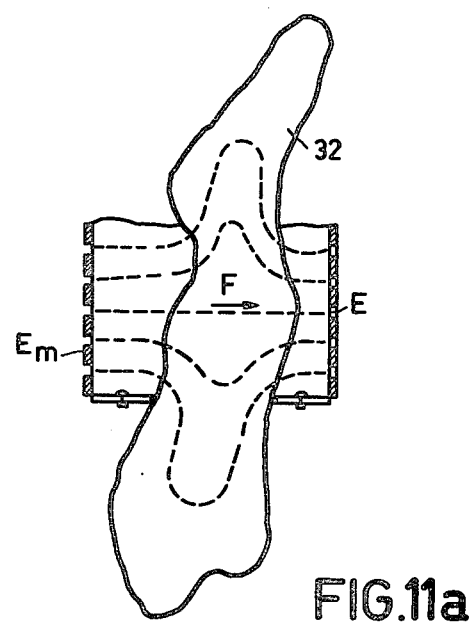
Figure 11B:
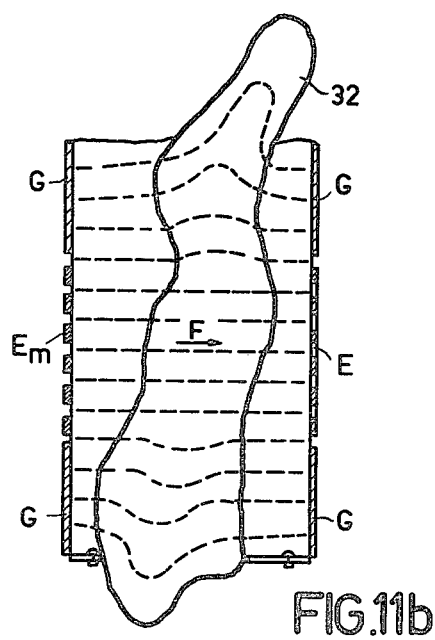
Figure 12:
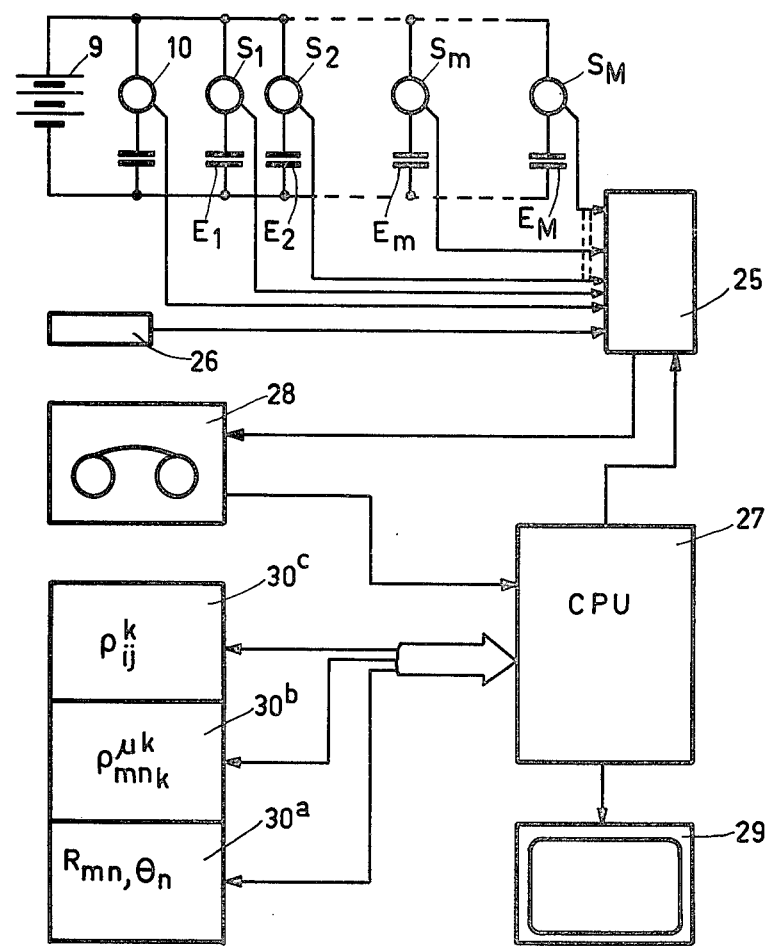
Figure 13:
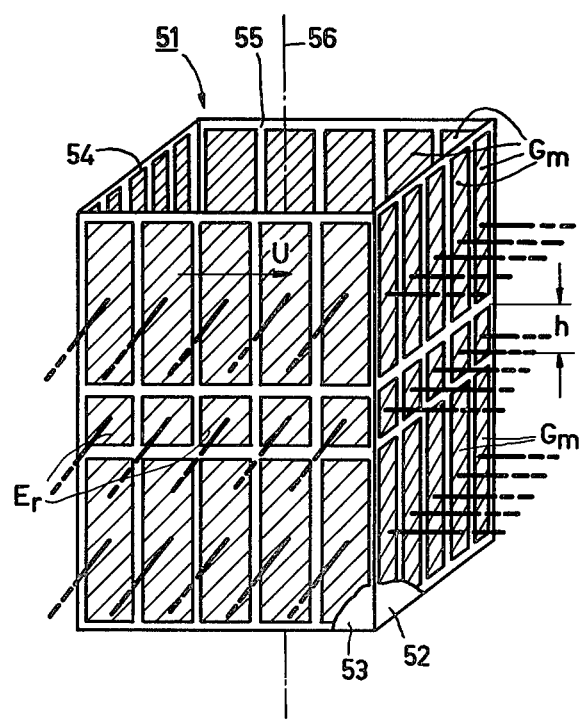
Figure 14:
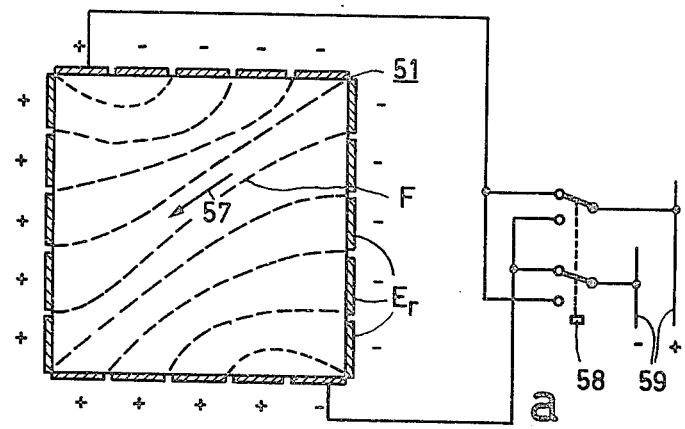
Figure 14:
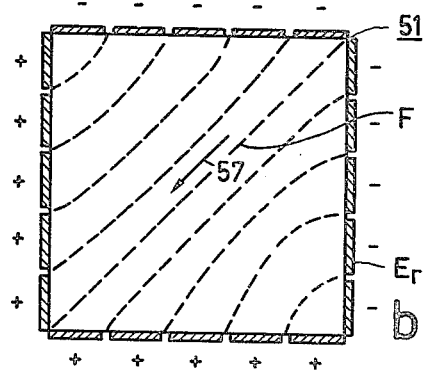
Figure 14:
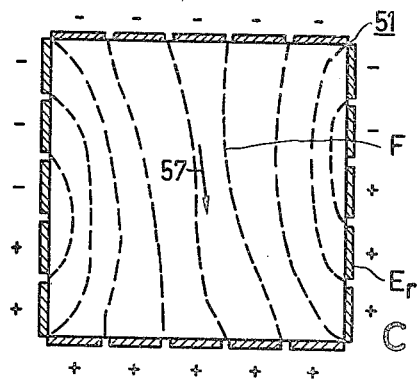
Figure 16:
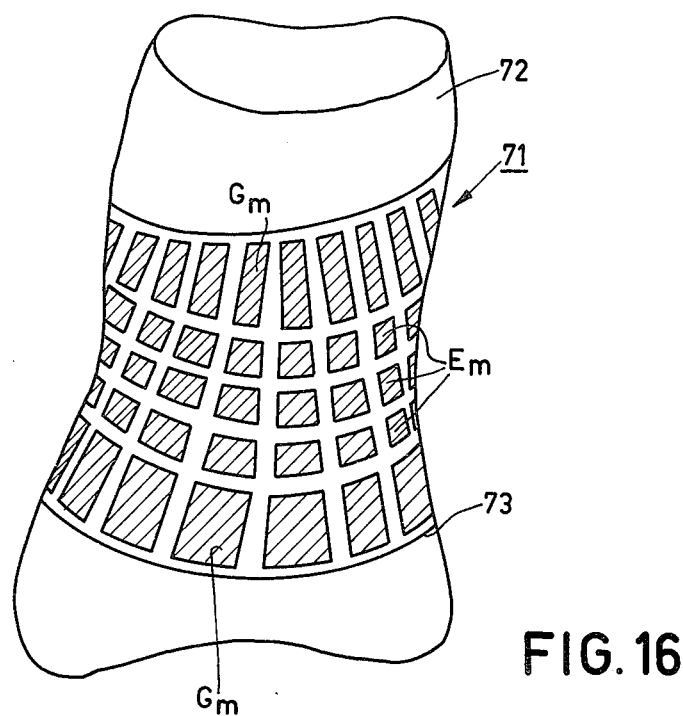
Figure 15:
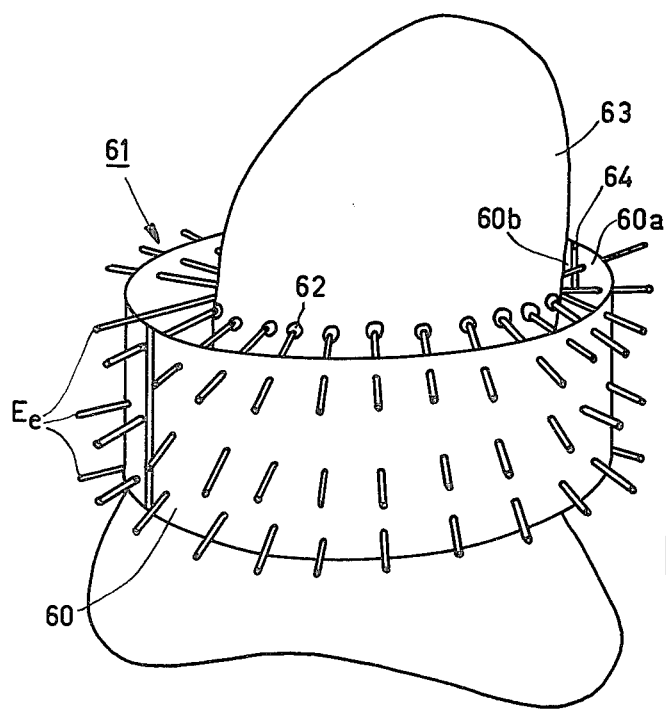

FIG. 5 shows a network, formed by equipotential lines and field lines, in a plane in an electrode array in accordance with FIG. 1, FIG. 6 shows, at an increased scale, a mesh of the network formed by equipotential lines and field lines of FIG. 5, FIG. 7 shows a matrix which is permanently related to the body to be examined and which is situated in the plane subject to the electric field, FIG. 8 illustrates an interpolation to be used for the method, FIG. 9 illustrates a further interpolation, FIG. 10 shows a box-like electrode array, FIGS. 11a and 11b each are a sectional view of an electrode array in which a body is arranged in order to illustrate the course of the electrode field lines, FIG. 12 is a block diagram of a device for performing the method in accordance with the invention, FIG. 13 shows a ring-like electrode array, FIGS. 14a, b, c each show a plane which is subject to an electric field in a box-like electrode array, the field occupying different directions in the plane, FIG. 15 shows a cylindrical array which is to be arranged around a body and which comprises individual electrodes to be arranged on the body, and FIG. 16 shows an elastic electrode array which is to be arranged closely against the body.

The method of determining a structural distribution of a body will be described in detail hereinafter on the basis of a two-dimensional example. The method can be readily extended to three dimensions by taking into account each time the associated third coordinate in the following equations.

FIGS. 1 to 9 serve for the description of the method. The plane of the body to be examined is surrounded by an electrode array which is situated in two parallel planes, so that the plane of the body to be examined is situated completely in the electric field extending between the electrodes of the electrode array. The electrode array comprises individual, adjacently arranged electrodes, the position of which in the plane is at least approximately known, so that tubes of flux are generated in accordance with the dimensions of the individual electrodes, said tubes being adjacently situated inside the body. The body is successively exposed to an electric field which is generated in different directions in the plane, so that currents are generated and measured in the individual tubes of flux. From the currents measured, electric resistance values are determined in the various tubes of flux, wherefrom subsequently the specific resistance is determined in individual elements of a matrix which is permanently related to the body and which is situated in the plane exposed to the electric field. The determination of the specific resistance will be described in detail hereinafter. The dimensions of the tubes of flux and hence the resolution of the electrode array are determined by the surface area of the individual measuring electrodes.

FIG. 1 shows a box-like electrode array which comprises a tank 1 which is to be filled with an electrolyte and whose walls 2, 3, 4, 5 and bottom 6 are made of an electrically insulating material. The electrode array consists of a strip-like electrode E which is arranged against the inner side of the rear wall 5 and which corresponds to the dimensions of the rear wall 5 and of various individual, rectangular electrodes $E_m$ are equally large and which are arranged against the inner side of the front wall 3. The individual electrodes $E_m$ cover the front wall 3 and are electrically insulated with respect to each other. The number of individual measuring electrodes $E_m$ amounts to M. In this example, M has the value eight. The walls 2,3, 4 and 5 each have a length 2r and a height h.

Furthermore, a rectangular coordinate system $[\xi, \eta, \zeta]$ is permanently related to the tank 1, the coordinate axes thereof extending perpendicularly through the walls 2, 3, 4 and 5 and the bottom 6, the origin 7 of said coordinate system being situated in a centre of the tank 1. The $\xi$-direction extends parallel to the electrode E and the $\zeta$-direction extends perpendicular to the bottom 6.

Figure 2:
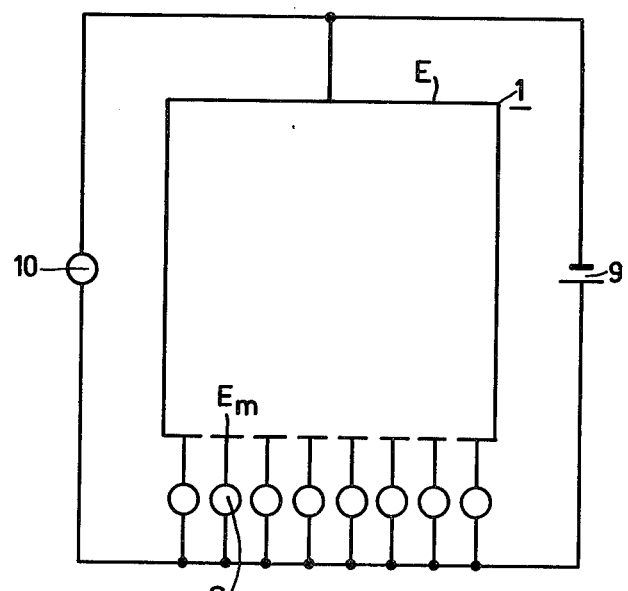
FIG. 2 is a plan view of the electrode array shown in FIG. 1 with electrical measuring and power supply elements.

FIG. 2 is a plan view of the tank 1. The individual measuring electrodes $E_m$ are each connected in series to current measuring apparatus $S_m$ which have a low internal resistance and which are all connected, via a voltage source 9, to the electrode E. Electrically parallel connected to the voltage source 9 is a voltage measuring apparatus 10 which measured approximately the electric voltage drop U between the strip-like electrode E and the individual measuring electrodes $E_m$. (Further circuit components have been omitted for the sake of simplicity).

Figure 3:
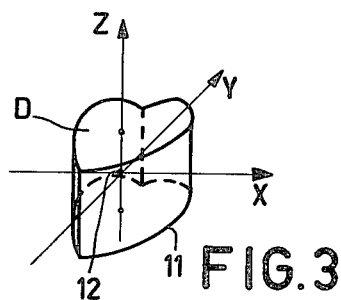
FIG. 3 shows a hypothetical body to be examined.

FIG. 3 shows a body 11 to be examined which is to be arranged in the tank 1 and which is situated in the origin 12 of a Cartesian coordinate system [x, y, z] which is permanently related thereto. The body 11 is shaped so that the geometry does not change in the z-direction. Furthermore, it is assumed that the specific resistance $\rho(x, y, z)$, capable of assuming values in the range $0 < \rho(x, y, z) < \infty$, is at least approximately independent of the z-direction and of electric and magnetic fields. The height of the body 11 in the z-direction corresponds to the height h of the tank 1.

Figure 4:
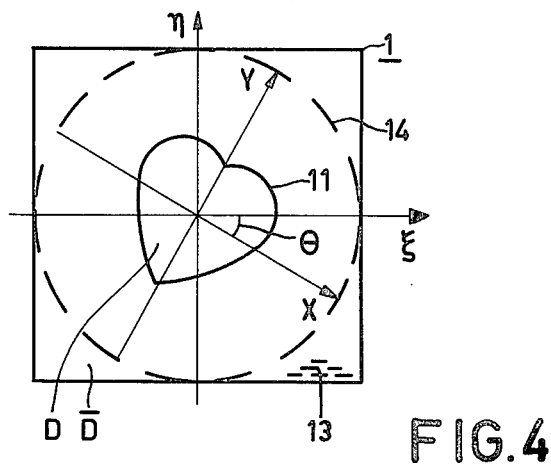
FIG. 4 shows and electrode array with a body to be examined.

FIG. 4 is a sectional view of the tank 1 in the $\xi$-$\eta$ plane of the coordinate system $[\xi, \eta, \zeta]$ which is associated with the tank 1. The body 11 to be examined is arranged inside the tank 1 so that the origins 7, 12 and the $\zeta$ and z-directions of the two systems of coordinates $[\xi, \eta, \zeta]$, [x, y, z], respectively, coincide. The body 11 can be rotated with respect to the tank 1 in that either the body 11 is rotated around the z-axis in the stationary tank 1, or in that the tank 1 is rotated around the z-axis whilst the body 11 is stationary. The $\xi$ and x-directions then enclose an angle $\theta$ which always indicates the position of the body 11 with respect to the tank 1. The electrolyte 13, having a specific resistance $\rho_b$ is present around the body 11. The electrolyte 13 is chosen so that the specific resistance $\rho_b$ thereof at least approximately corresponds to the specific resistance $\rho(x, y, z)$ of the body 11. The circle 14 denoted by a broken line in the tank 1 bounds the largest area which may be occupied by a body 11 during a relative movement between the body and the tank 1. The area occupied by the body 11 in the $\xi$-$\eta$ plane will be referred to as the object area D hereinafter.

Using the assumptions made concerning the z-independency of contour geometry and specific resistance $\rho(x, y, z)$ of the body 11, the problem has been reduced to two dimensions, so that hereinafter it is merely necessary to consider only the relationships in the $\xi$-$\eta$ plane of the coordinate system $[\xi, \eta, \zeta]$ permanently associated with the tank 1. Such a consideration of the problem is possible for a very small height h of the tank.

For determining the two-dimensional structural distribution in the object area D of the body 11, a voltage U is applied between the strip-like electrode E and the individual measuring electrodes $E_m$ ($E_1, \ldots, E_M$). For each tube of flux 17, defined by the dimensions of the electrodes $E_m$ (FIG. 5), the electric current $I_{m\theta}$ flowing therethrough is measured, said current being dependent of the $m^{th}$ measuring electrode $E_m$ and of the angle $\theta$ which indicates the position of the body 11 with respect to the tank 1.

Thus, a so-termed current projection ($I_{1\theta} \ldots I_{M\theta}$) for an angle $\theta$ is obtained. The vector ($R_{1\theta} \ldots R_{M\theta}$) then represents the associated resistance projection for the angle $\theta$ at which an individually measured resistance value $R_{m\theta} = U/I_{m\theta}$. In order to enable accurate determination of the distribution of the specific resistance $\rho(x, y, z)$ in the area D of the object, it is necessary to record resistance projections at different angles $\theta_n$. Thus, a set of resistance projections is obtained:

$$R_{11}, \ldots R_{M1}; \qquad (1)$$
$$R_{12}, \ldots R_{M2};$$
$$\vdots$$
$$R_{1N}, \ldots R_{MN};$$

associated with a set of angles $\theta_n$, where $n = 1, \ldots, N$. Hereinafter, the angle $\theta_n$ is only referred to as n, $\theta_n$ assuming values in the range $0 \leq \theta_n < 2\pi$. The invention has for its object to determine the specific resistance $\rho(x, y, z)$ in the object area D of the body 11 by means of these resistance projections. To this end, a given (assumed) resistance distribution within the object area D is required, as will be explained hereinafter.

FIG. 5 again shows the $\xi$-$\eta$ plane extending through the tank 1. When a voltage U is applied between the strip-like electrode E and the individual measuring electrodes $E_m$, a network 16 consisting of electric field lines 14 and equipotential lines 15 is imagined in the tank 1, in accordance with the distribution of the specific resistances $\rho_b$ and $\rho(x, y, z)$ of the electrolyte 13 and the body 11. Two field lines 15 each time enclose a tube of flux 17.

For determining calculated resistance values $R_{mn}{}^i$, it makes sense to subdivide a tube of flux 17 into different meshes $Q_{mn}{}^\mu$, each mesh $Q_{mn}{}^\mu$ being bounded by two equipotential lines 15 and two field lines 14. The number of meshes may be chosen to correspond to the number of electrodes $E_m$, each mesh $Q_{mn}{}^\mu$ having a mesh resistance $R_{mn}{}^\mu$, $\mu$ being the number of mesh in a tube of flux 17 ($0 \leq \mu \leq M$). The resistance value $R_{mn}{}^i$ for each tube of flux 17 is then found by summing the mesh resistances $R_{mn}^\mu$ of all meshes $Q_{mn}^\mu$, where $R_{mn}^i = \Sigma_\mu R_{mn}^\mu$ and $\mu = 1, \ldots, M$.

FIG. 6 is a representation at an increased scale of a mesh $Q_{mn}^\mu$ with an arrow 18 which indicates the field direction. The mesh $Q_{mn}^\mu$ is bounded by two field lines 14 and two equipotential lines 15 which intersect at the corner points $P_1$, $P_2$, $P_3$, $P_4$ of the mesh. A rectangle 19, having a width $w_{mn}^\mu$ and a length $l_{mn}^\mu$ is arranged across the mesh $Q_{mn}^\mu$. The determination of the resistance data can thus be substantially simplified. Taking into account the small height h of the tube of flux 17, the following expression is obtained for a tube of flux 17:

$$R_{mn}^i = \sum_{\mu=1}^{M} \frac{l_{mn}^\mu}{w_{mn}^\mu} \frac{\rho_{mn}^\mu}{h} \quad (2)$$

Therein, the mesh resistance $R_{mn}^\mu$ is given by the specific resistance $\rho_{mn}^\mu$ at the point $P_{mn}^\mu$, the point $P_{mn}^\mu$ being situated in the centre of the rectangle 19.

The rectangle 19 is formed as follows. Two corner points $P_1$, $P_2$, $P_3$, $P_4$ of the mesh are interconnected by a straight lines on which points $P_{12}$, $P_{23}$, $P_{34}$, $P_{14}$ are indicated which are situated halfway between two corner points $P_1$, $P_2$, $P_3$, $P_4$ of the mesh. The sides of the rectangle 19 are arranged through the points $P_{12}$, $P_{23}$, $P_{34}$ and $P_{14}$.

Taking into account that the body 11 is situated only in the area D of the object, the resistance value $R_m$ for each tube of flux 17 amounts to:

$$R_{mn}^i = \sum_{\mu \in \overline{D}} \frac{l_{mn}^\mu}{w_{mn}^\mu} \frac{\rho_b}{h} + \sum_{\mu \in D} \frac{l_{mn}^\mu}{w_{mn}^\mu} \frac{\rho_{mn}^\mu}{h} \quad (3)$$

Therein, the outer region $\overline{D}$ (FIG. 4) of the tank 1 which surrounds the object area D contains the electrolyte 13 having a specific resistance $\rho_b$. It is to be noted that neither the length $l_{mn}^\mu$, nor the width $w_{mn}^\mu$, nor the specific resistance $\rho_{mn}^\mu$ or the location of the point $P_{mn}^\mu$ are known, because the course of the field lines 14 and the course of the equipotential lines 15 in the tank 1 is unknown.

In order to solve the problem concerning the specific resistance $\rho_{mn}^\mu$, the x-y plane of the system of coordinates x, y, z relates to the body 11 is covered by a matrix P as shown in FIG. 7. A raster P of this kind also has a fixed positional relation with respect to the body 11. The individual points $P_{ij}$ in the matrix P have the coordinates $(i\Delta, j\Delta, 0)$ and are the centres of the elements $\epsilon_{ij}$. Therein, $\Delta = 2r/M$ and i and j are a running index (i, j = $-M/2, \ldots$ 1, 0, 1, 2 $\ldots$ $+M/2$). In the elements $\epsilon_{ij}$ it is then possible to define new specific resistance $\rho_{ij}$ which are unknown per se but which can be readily determined. Each point $P_{mn}^\mu$ (FIGS. 5,6) is surrounded by four points $P_{ij}$, so that an approximate specific resistance $\tilde{\rho}_{mn}^\mu$ at the point $P_{mn}^\mu$ can be determined by bilinear interpolation from the specific resistance $\rho_{ij}$. Of course, this is necessary only in the object area D, because the specific resistance $\rho_b$ in the outer region $\overline{D}$ in any location is known.

FIG. 8 serves to illustrate the bilinear interpolation. At a point $\tilde{P}$ (for example, $P_{mn}^\mu$), the specific resistance $\rho_{mn}^\mu$ is to be determined. The point $\tilde{P}$ obtains the assumed coordinates $(\tilde{x}, \tilde{y}, 0)$ within the object area D. First a pair of indices i, j is determined for which the relation $x_i \leq \tilde{x} \leq x_{i+1}$ and $y_j \leq \tilde{y} \leq y_{j+1}$ is applicable. Thus, the four points $P_{ij}$ of the matrix P surrounding $(\tilde{x}, \tilde{y}, 0)$ are determined. Subsequently, $\tilde{\rho}_{mn}^\mu$ is determined in accordance with the equation:

$$\tilde{\rho}_{mn}^\mu = (1-\alpha) \cdot (1-\beta) \cdot (\rho_{i,j} + \beta \rho_{i,j+1}) + \quad (4)$$
$$\alpha \cdot ((1-\beta) \cdot \rho_{i,j+1} + \beta \cdot \rho_{i+1,j+1})$$

Therein, $\alpha = (x - x_i)/\Delta$ and $\beta = (y - y_j)/\Delta$. In the vicinity of the edge of the object area D, some points: $P_{ij}$; $P_{i+1,j}$, $P_{i,j+1}$; $P_{i+1,j+1}$ may be situated outside the object area D. In that case the specific resistance $\rho_{mn}^\mu$ is assumed to be equal to the specific resistance $\rho_b$ of the electrolyte 13.

The length $l_{mn}^\mu$ and the width $w_{mn}^\mu$ of the rectangle 19 and the coefficients $\alpha, \beta$ are dependent of the course of the field lines 14 and the equipotential lines 15 in the system of coordinates $[\xi, \eta, \iota]$, the course again being determined by the distribution of specific resistance $\rho(x, y, z)$ of the body 11 which encloses an angle $\theta_n$ with respect to the tank 1. Even though the distribution of specific resistance $\rho(x, y, z)$ in the body 11 is unknown, the length $l_{mn}^\mu$, the width $w_{mn}^\mu$ and the coefficients $\alpha$ and $\beta$ can be determined if a specific resistance $\rho_{ij}$ is given at the points $P_{ij}$ of the object area d of the matrix P permanently related to the body 11. The values of the specific resistance $\rho_{ij}$ are continued, by linear interpolation, to a function in the x-y plane, wherefrom a function of a specific resistance $\rho_{\theta n}$, defined in the $\xi$-$\eta$ plane, can be determined by means of a simple coordinate transformation. Using known electrostatics equations and taking into account the secondary conditions, the approximate course of the field lines 14 and equipotential lines 15 in the $\xi$-$\eta$ plane can be determined from the function of this specific resistance $\rho_{\theta n}$, it being possible to determined the length $l_{mn}^\mu$ and the width $w_{mn}^\mu$ and the coefficients $\alpha$ and $\beta$ from this course. Of course, this is applicable to each angle $\theta_n$ and to each set of specific resistances $\rho_{ij}$ and each set of points $P_{ij}$ of the elements $\epsilon_{ij}$ of the matrix P.

Only the specific resistance $\rho_{ij}$ at the points $P_{ij}$ of the matrix P is known. However, this can be given in advance, for example, by assuming it to be equal at all points $P_{ij}$ to the specific resistance $\rho_b$. The first approximation of the specific resistance $\rho_{ij}$ is then stepwise improved, in that each time for all tubes of flux 17 the calculated resistance values $R_{mn}^i$ are compared with the measured resistance values $R_{mn}$ for correction of the specific resistance $\rho_{ij}$, correction values $\Delta \rho_{ij}$ for $\rho_{ij}$ being determined therefrom.

Assume that the method has proceeded to the step k (k = integer number). In this $k^{th}$ step, a distribution of the specific resistance $\rho_{ij}^k$ (at the points $P_{ij}$ of the matrix P) is given in advance. The aim is then to obtain the distribution of the specific resistance $\rho_{ij}^{k+1}$ for the beginning of the $(k+1)^{th}$ step. Furthermore, an angle $\theta_{nk}$ is chosen at which the body 11 extends with respect to the tank 1, so that the data $\rho_{ij}^k$ and $\theta_{nk}$ can be determined from the course of the field lines 14 and the course of the equipotential lines 15 by using known electrostatic equations and taking into account the secondary conditions (the voltage applied to the electrodes). From the course of the field lines and equipotential lines, a set of cross-points $$[\xi_{mnk}^{\mu k}, \eta_{mnk}^{\mu k}; \text{ in which } m, \mu = 0, 1, \ldots, M]$$

of field lines 14 and equipotential lines 15 is derived; therefrom the length $l_{mnk}{}^{\mu k}$, the width $w_{mnk}{}^{\mu k}$ and the point $P_{mnk}{}^{\mu k}$ of a rectangle assumed on a mesh $Q_{mnk}{}^{\mu k}$ (see FIG. 6) can be readily derived. The cross-points $[\xi_{mnk}{}^{\mu k}, \eta_{mnk}{}^{\mu k}]$ then correspond to the corner points $P_1$, $P_2$, $P_3$, $P_4$ of the mesh in FIG. 6.

Subsequently, the specific resistance $\rho_{mnk}{}^{\mu k}$ at point $P_{mnk}{}^{\mu k}$ is determined from $\rho_{ij}{}^k$ by bilinear interpolation. The bilinear inerpolation has already been described with reference to FIG. 8. Using these data, the resistance values $R_{mnk}{}^k$ can be determined in the $k^{th}$ step via the following calculation:

$$R_{mnk}^k = \sum_{\mu \epsilon D} \frac{1_{mnk}^{\mu k}}{w_{mnk}^{\mu k}} \frac{\rho b}{h} + \sum_{\mu \epsilon D} \frac{1_{mnk}^{\mu k}}{w_{mnk}^{\mu k}} \frac{\rho_{mnk}^{\mu k}}{h} \quad (5)$$

in which m extends from 1 up to and including M.

Hereinafter, various calculated resistance values $R_{mnk}{}^k$ in general fo the measured resistances $R_{mnk}$ will be given. Therefore, for each point $P_{mnk}{}^{\mu k}$ of the object area D a correction $\Delta\rho_{mnk}{}^{\mu k}$ for the previously determined specific resistance $\rho_{mnk}{}^{\mu k}$ is determined. This correction is directly proportional to the length $1_{mnk}{}^{\mu k}$ and inversely proportional to the width $w_{mn}{}^{\mu k}$. The proportionality factor is determined via a formula as follows:

$$\frac{\Delta\rho_{mnk}^{\mu k}}{h} = \frac{R_{mnk} - R_{mnk}^k}{\sum_{\mu \epsilon D} \frac{1_{mnk}^{\mu k}}{w_{mnk}^{\mu k}}} \cdot \frac{1_{mnk}^{\mu}}{w_{mnk}^{\mu k}} \quad (6)$$

Thus, for the $(k+1)^{th}$ step a distribution of the specific resistance $$\rho_{mnk}^{\mu k+1} = \rho_{mnk}^{\mu k} + \Delta\rho_{mnk}^{\mu k}$$

is obtained for the points $P_{mnk}{}^{\mu k}$ in the meshes $Q_{mnk}{}^{\mu k}$.

However, it is important to determine the change $\Delta\rho_{ij}{}^k$ of the specific resistance $\rho_{ij}{}^k$ in the elements $\epsilon_{ij}$ of the matrix P in the object area D. The change $\Delta\rho_{ij}{}^k$ is determined by interpolation between the corrections $\Delta\rho_{mnk}{}^{\mu k}$ is obtained.

FIG. 9 illustrates the interpolation method. A point $P_{ij}$ in the object area D is given. First a polygon $Q_{mnk}{}^{\mu k}$, comprising corner points $P_{mnk}{}^{\mu k}$, $P_{m+1,nk}$, $P_{m+1,nk}{}^{(\mu+1)k}$ and $P_{m,nk}{}^{(\mu+1)k}$, wherebetween $P_{ij}$ is situated, is searched. Subsequently, the position of the points $\tilde{P}_1$ and $\tilde{P}_2$ is determined by extending two lines a and b so that they intersect in a point c. Through the points c and $P_{ij}$ a third line is drawn whose points of intersection with lines e and f determine the position of the points $\tilde{P}_1$ and $\tilde{P}_2$. Linear one-dimensional interpolation in the direction of the lines e and f is used to determine the intermediate values $\Delta\rho_{p1}$, and $\Delta\rho_{p2}$ and therefrom the change $\Delta\rho_{ij}{}^k$ by linear one-dimensional interpolation again. If the polygon $Q_{mnk}{}^{\mu k}$ is a rectangle, the preceding interpolation is reduced to a normal bilinear interpolation. The $k^{th}$ step has been completed after calculation of the new specific resistance $\rho_{ij}{}^k{}^{+1} = \rho_{ij}{}^k + \Delta\rho_{ij}{}^k$ for all i and j which are associated with the elements $\epsilon_{ij}$ which are situated in the object ar D. For the next step a new angle $\theta_{nk+1}$ is chosen which effectively deviates of from 45° to 90° from the angle $\theta_{nk}$. The calculations may be interrupted, for example, after a given number of iterations k, for example, the measuring values measured at all angles $\theta_n$ being used a corresponding number of times in the calculation.

FIG. 10 is a broken-away view of a box-like tank 31 by means of which a body 32 to be examined can be examined in different planes 20 which are denoted by broken lines. A plane 20 is the $\xi\eta$ plane or the x-y plane described with reference to FIG. 4. On the inner side of the tank wall 33 there are provided various strip-like electrodes E which have a height h and whose longitudinal direction L extends perpendicular to the symmetry axis 21 of the tank 31 which is assumed to be the axis of rotation. The axis of rotation 21 is actually the $\zeta$ or z-axis shown in the FIGS. 1 and 3, respectively. On the tank wall 34 (only partly shown) which is situated opposite the tank wall 33 there are provided similarly arranged but individual measuring electrodes $E_m$, so that an electrode field consisting of rows and columns is formed. Between the strip-like electrodes E and the measuring electrodes $E_m$ a flat electric field is produced when an external voltage is applied, the direction of said field being represented by the arrow 22. Above and below the electrodes E and the measuring electrodes $E_m$ there are provided further strip-like guard electrodes G which are arranged in the same way as the strip-like electrodes E in order to ensure that the field F between the electrodes E and $E_m$ does not expand in the direction of the axis 21. At the upper side and the lower side of the tank 1 there is provided an elastic cover 23 with an aperture 25 and a collar 24 wherethrough a body 32 to be examined can be introduced into the tank 1. The elastic cover 23 should comprise rotatable seals (not shown) so that the collar 24, flatly contacting the body 32 so that the electrolyte 35 surrounding the body 32 cannot escape from the tank 31, can be stationary whilst the tank 31 rotates. It is to be noted that all electrodes E and guard electrodes G carry the same potential.

A further embodiment of the tank 31 comprises a single electrode plate (not shown) which is arranged on the inner side of the tank wall 33 and completely covers this wall and which comprises all strip-like electrodes E and guard electrodes G.

In order to obtain an approximation where the contour of the body 32 or the specific resistance $\rho(x, y, z)$ thereof may be independently considered in the z-direction (longitudinal direction of the axis of rotation 21), the height h of the measuring electrodes $E_m$ and of the strip-like electrodes E should be small accordingly.

The function of the guard electrodes G will be described with reference to the FIGS. 11a and b. In the absence of guard electrode G (FIG. 11a), the field F (field lines denoted by broken lines) present between the electrode E and the electrodes $E_m$ at the area of the body 32 will expand beyond the electrodes E and $E_m$. As a result of the use of guard electrodes G (FIG. 11b), the field F at the area of the individual electrodes $E_m$ is maintained at least approximately in the plane between the electrodes E and $E_m$.

FIG. 12 shows an embodiment of a device for performing (in cooperation with, for example, the measuring tank shown in FIG. 10) the method in accordance with the invention. The voltage source 9, the voltmeter 10, the ammeters $S_1$, $S_2$, ... $S_m$, and the measuring electrodes $E_1$, $E_2$, ... $E_m$ ... $E_M$ shown in FIG. 10 form a measuring system whose outputs which carry measuring values are all connected to a first processing circuit 25 which may comprise, for example, an analog multiplex circuit and an analog/digital converter The circuit 25 has connected to it an angle measuring device 26 which supplies a measuring value which is directly proportional to the angular shift of the tank 31 with respect to the stationary body 32 to be examined. The angle measuring device 26 may be, for example, a multiturn potentiometer which is mechanically coupled to the tank 31 in known manner.

Under the control of a central processor unit 27, the measuring values applied to the circuit 25 are stored in a magnetic tape memory 28 in digital form. After all measuring values have been collected, the central processor unit 27 calculates the values $R_{mn}$ and $\theta_n$ which are stored in a first storage section 30a.

Using given specific resistance values $\rho_{ij}$, stored in advance in a second storage section 30c, the course of a number of field lines and equipotential lines occurring in a plane 20 defined by the tank 31 are calculated for an angle $\theta_n$ to be selected (from storage section 30a), the number of field lines (M) being determined by the number of measuring electrodes $E_M$. The number of equipotential lines is preferably chosen to equal M. From the cross-points of the field and equipotential lines to be determined, the dimensions (for example, length $l/_{mnk}{}^{\mu k}$, width $w/_{mnk}{}^{\mu k}$) are derived for the meshes $Q/_{mnk}{}^{\mu k}$ which are enclosed by the field lines and equipotential lines. By interpolation of the dimensions of the meshes $Q/_{mnk}{}^{\mu k}$ and the given $\rho_{ij}$, significant resistance values $\rho/_{mnk}{}^{\mu k}$ are obtained for the meshes, said specific resistance values being stored in a storage section 30b together with the dimensions of the meshes. The coordinates of the corner points (the cross-points of the field and equipotential lines) are also stored in the storage section 30b. If the capacity of the storage section 30b is to be limited, it is alternatively possible to store only said coordinates; in that case, however, distances between the coordinates must each time be calculated again for each calculation.

Using the dimensions and specific resistance values $\rho/_{mnk}{}^{\mu k}$ stored in the storage section 30b, a resistance value $R_{mnk}{}^k$ is calculated for each tube of flux by means of the formula (5). Subsequently, after the fetching of the values $R_{mn}$ from the storage section 30a and the dimensions of the various meshes $Q/_{mnk}{}^{\mu k}$ is from the storage section 30b, a correction resistance distribution $\Delta\rho/_{mnk}{}^{\mu k}$ is determined by means of the formula (6). The correction resistance distribution $\Delta\rho/_{mnk}{}^{\mu k}$ is stored in the storage section 30b at the location of the specific resistance value $\rho/_{mnk}{}^{\mu k}$. Subsequently, the values $\Delta\rho/_{mnk}{}^{\mu k}$ (see FIG. 9 and associated description) are interpolated to form a correction $\Delta\rho_{ij}{}^k$ which is added to the previous value $\rho_{ij}{}^k$. The sum is the new specific resistance $\rho_{ij}{}^{k+1}$ which is stored in the storage section 30c. After a sufficient number of iterations have been performed for each measuring direction $\theta$ n, the calculated specific resistance values $\rho_{ij}{}^{k+1}$ can be displayed on a display device 29. If necessary, these values can be recorded e.g. in a punched tape (not shown) or on a magnetic disc memory. After calculation of all $\rho_{ij}{}^{k+1}$, a next measuring direction $\theta_n$ is chosen for which the field and equipotential lines are again calculated on the bases of the corrected $\rho_{ij}{}^{k+1}$. After all measuring values $R_{mn}$ of each measuring direction $\theta_n$ have been used, the measuring values $R_{mn}$ of a previously treated measuring direction $\theta_n$ can be used again, using the $\rho_{ij}{}^{k+1}$ corrected thus far.

The number of iterations to be performed for each measuring direction $\theta_n$ may be indicated in advance, but it may also be made dependent of the difference between the measured resistance values $R_{mn}$ and the calculated resistance values $R_{mnk}{}^k$.

FIG. 13 shows a tank 51, the walls 52, 53, 54, 55 of which support a strip-like ring of electrodes $E_r$ on their inner side, said ring having a limited height h and being arranged in a plane (FIG. 10) which extends perpendicularly to the axis of rotation 56. Each of the electrodes $E_r$ may be connected to a positive or a negative pole of a voltage source as desired. Above and below the individual electrodes $E_r$ each time individual rectangular guard electrodes $G_m$ are provided, the width in the direction U thereof corresponding to the width of the individual electrodes $E_r$. Pole reversal of individual electrodes $E_r$ and associated guard electrodes $G_m$ enables the direction of the field F generated between the electrodes $E_r$ can be changed with respect to a body to be arranged in the tank 51 without relative movement between tank 51 and the body. The change of the polarity of the guard electrodes $G_m$ should each time correspond to that of the individual electrodes $E_r$.

FIGS. 14a, b, c are sectional views through the individual electrodes $E_r$, perpendicularly to the axis of rotation 56 of the tank 51. Two coherent groups of individual electrodes $E_r$ have a positive or a negative polarity. By changing the polarity of one of the outer individual electrodes $E_r$ of each group, the direction 57 of the field F with respect to the tank 51 or with respect to the body (not shown) can be rotated through an angle which is determined by the dimensions of the electrode. In the vicinity of the tank wall 52, 53, 54, 55, only a "shift" of the field F occurs, because the field always extends perpendicularly to the surface of the individual electrodes $E_r$, so that the object area D (FIG. 4) should be chosen smaller accordingly.

Obviously, the tank 51 may also be shaped as a circle cylinder, so that the maximum permissible object area D (FIG. 4) may be larger.

The changing of the direction 57 of the electric field F is realized by pole reversal of the individual electrodes $E_r$, each of which is connected to switching means 58 (shown only for two electrodes), said switching means being connected to power supply lines 59. The supply lines 59 are connected to a voltage source (for example, as shown in FIG. 10). Activation of the switching means 58 causes pole reversal of the electrodes $E_r$ connected thereto, so that an electric field F is generated as shown in FIG. 14b.

Obviously, the switching means 58 may be not only manual switches, as shown, but may also consist of electromagnetic or semiconductor switches, so that a substantially higher switching speed can be obtained. It is thus possible on the one hand to reduce the measuring time (time necessary for measuring in each feasible field with a different direction) and on the other hand, utilizing an accurately stabilized direct voltage source, and still operating the electrode array with "alternating voltage" (by a high switching frequency of the switching means) in order to avoid polarization of an object arranged between the electrodes.

FIG. 15 shows a rigid, cylindrical ring 60 of a tank 61, formed as a hollow cylinder, which is provided with single electrodes $E_e$. The single electrodes $E_e$ are rod-shaped, and one end thereof comprises a contact area 62 which is arranged directly on the surface of the body 63 to be examined. To this end, the single electrodes $E_e$ are arranged on the ring 60 to be displaceable in the radial direction with respect to the body 63. All single electrodes $E_e$ also comprise measuring elements (not shown) which determine the displacement of the single electrodes $E_e$ and hence the position of the contact areas 62. The guard electrodes which are situated above and below the single electrodes $E_e$ and which are shaped and arranged on the ring 60 in the same way as single electrodes $E_e$, have been omitted for the sake of clarity.

The ring 60 consists of two separate ring halves 60a and 60b which are rotatable about a connection shaft 64, so that the ring can be arranged around the body 63.

In FIG. 16, the tank 71 is shaped as an elastic hollow cylinder 73 which is to be arranged flatly against the body 72 and the inner side of which supports individual electrodes $E_m$ as well as guard electrodes $G_m$ which are also made of an elastic, electrically conductive material. The arrangement of the individual electrodes $E_m$ as well as of the guard electrodes $G_m$ corresponds to that of the electrodes $E_r$ and $G_m$, respectively, of the tank 51 described with reference to FIG. 13 which is constructed as a rigid, square cylinder.

When a body to be examined consists of a dielectric which is substantially not conductive, the described method can be used, for example, to determine a flat distribution of a dielectric constant of the body (for example, material tests), preferably by means of a tank 51 as described with reference to FIG. 13, by applying a high frequency alternating voltage to the individual electrodes $E_r$. Capacitance projections (projection of apparent resistances) ($x_{10}, \ldots x_{M\theta}$), where $x_m$ is $U/I_m = 1/(2.f.C_m)$, corresponding to "resistance projections" ($R_{1\theta} \ldots R_{M\theta}$), can be determined by measuring the currents flowing through the electrodes $E_r$ or the electric voltages present therebetween. In that case, no conductive electrolyte 13 need be present between the tank walls 52, 53, 54, 55 and a body to be examined. The determination of the flat distribution of the dielectric constants is then realized in the already described manner.

What is claimed is:

1. A method of determining the internal structure of a body comprising the steps of:
   exposing the body to an electric field which extends between individual electrodes of an electrode array which at least partially surrounds the body;
   successively rotating the electric field through a plurality of different orientations with respect to the body;
   measuring electric currents which flow between the individual electrodes for each of the different orientations of the electric field;
   determining electrical resistance projections for individual tubes of current flux generated between the electrodes for each of the orientations of the electric field from the measurements of electrical current; and
   determining the value of electrical resistance in individual elements of an imaginary matrix defined over the body by;
   (a) assuming a specific distribution of resistance over the matrix elements;
   (b) calculating an approximate distribution of field lines and equipotential lines within the body for each orientation of the field on the basis of the assumed distribution of resistance;
   (c) calculating an approximate resistance in each tube of flux on the basis of the approximate distribution of the field lines and the assumed distribution of resistance;
   (d) calculating a correction resistance distribution in each tube of flux by determination of the difference between the approximate resistance in that tube and the resistance projection determined from the measurement of the electric currents; and
   (e) calculating a correction value for the specific resistance value for each element from the correction resistance distribution by interpolation.

2. A method as claimed in claim 1 wherein the approximate resistance value for each tube of flux is calculated by:
   (a) subdividing each tube of flux into meshes which are bonded by equipotential lines;
   (b) determining the length and width dimensions of each mesh as defined by the cross-points of field lines and equipotential lines;
   (c) determining, for each mesh, an approximate resistance by interpolation between the assumed specific resistance values associated with matrix elements which at least partially coincide with that mesh; and
   (d) summing the approximate resistance of individual meshes associated with the tube of flux.

3. A method as claimed in claim 2 wherein calculating the correction resistance distribution in each tube of flux comprises the steps of:
   determining the difference between the measured value of a resistance projection and the calculated approximate resistance value and
   determining a mesh correction which is directly porportional to the difference and to the length of the associated mesh; and is inversely porportional to the width of the associated mesh and to the sum of the squares of the quotients of the length and the width of each mesh in the tube of flux.

4. A method as claimed in claim 1, 2, or 3 wherein the step of rotating the electric field comprises rotating the electrode array around an axis extending through the body; the axis being directed transverse to the electric field generated between the electrodes, the position of the axis remaining unchanged with respect to each electrode during rotation.

5. A method as claimed in claim 4 wherein the electric field is produced by connecting an alternating electric voltage to one or more of the electrodes of the array.

6. A method as claimed in claim 1, 2 or 3 wherein the step of rotating the electric field comprises generating differently directed electric fields by reversing the polarity of individual electrodes in the electrode array; the position of the electrode array remaining unchanged with respect to the body during rotation.

7. A method as claimed in claim 6 wherein the electric field is produced by connecting an alternating electric voltage to one or more of the electrodes of the array.

8. A method as claimed in claim 1, 2, or 3 wherein the electric field is produced by connecting an alternating electric voltage to one or more of the electrodes of the array.

9. A device for determining the internal structure of a body comprising:
   an electrode array comprising a plurality of individual electrodes disposed to at least partially surround the body;

means for producing a potential difference between at least some of the electrodes to produce an electric field in the body;

measuring means connected to at least some of the electrodes for measuring currents flowing through individual electrodes, the measuring system functioning to measure currents flowing through individual electrodes at different orientations of the electric field with respect to the body, the currents being a measure of the electrical resistance values in tubes of flux generated between electrodes of different potential;

means for successively changing the orientation of the elelctric field with respect to the body;

first storage means for storing orientation values which are a measure of the orientation of the successive electric fields with respect to the body and for storing projections of the measured resistance values which are derived from currents measured at an associated orientation of the field;

second storage means for storing specific, assumed resistance values each of which is associated with one element of an imaginary matrix of elements defined over the body;

third storage means for the storage of further data; and central processor means for:

determining, for each orientation, electric field and equipotential lines which divide a space determined by the matrix into meshes from the assumed resistance value and the orientation values, and for storing values which are a measure of coordinates of the meshes in the third storage means;

determining, by interpolation, an approximate mesh resistance in each mesh from the specific resistance values in the elements and the coordinates of each mesh and for storing the approximate mesh resistances in the third storage means;

calculating a resistance value between two field lines by summation of mesh resistance values which are directly proportional to the approximate mesh resistance and to the length and inversely proportional to the width of the associated mesh;

determining, from the difference between the measured resistance value and the calculated resistance value for each field direction, a correction resistance distribution for each mesh which is directly proportional to the difference and to the length of the mesh and which is inversely proportional to the width of the mesh, and for storing the correction resistance value in the third storage means;

determining, by interpolation, from the stored correction resistance values a correction for the assumed resistance value in each elements; and adding the correction to the associated assumed resistance value and storing sums thus obtained in the second storage means.

10. A device as claimed in claim 9 wherein the electrode array is rotatable with respect to an axis which is transverse to the direction of the electric fields generated between the individual electrodes of the array and further comprising angle measuring means coupled to the electrode array for producing the orientation values.

11. A device as claimed in claim 10 further comprising a tank of insulating material having a square cross-section, the electrode array being disposed on inner walls of the tank, at least one inner wall of the tank being provided with a row of measuring electrodes which are insulated one from the other, at least one further electrode being formed on a wall opposite the row, the further electrode having dimensions parallel and perpendicular to the row of measuring electrodes which are equal to the overall dimensions of the row of electrodes.

12. A device as claimed in claim 9 further comprising a cylindrical tank of insulating material, the electrode array being formed on an inner wall of the tank, individual electrodes of the array being adjacently arranged in a ring-like array and electrically insulated one from another, the plane of the ring being directed transverse to the cylinder axis and further comprising means for selectively reversing the polarity of individual electrodes in the array.

13. A device as claimed in claim 12 wherein the electrode array comprises individual rod-shaped electrodes which are arranged in a rigid cylinder shape, the plane of the ring being directed transverse to the cylinder axis and the electrodes being displaceable with respect to the cylinder of insulating material in the direction of the axis; and further comprising means for selectively reversing the polarity of individual electrodes.

14. A device as claimed in claim 9 wherein the electrode array comprises an elastic band adapted to be disposed against the body and adjacent electrodes comprising an elastic, electrically conductive material which enclose the body; and further comprising switching means for reversing the polarity of individual electrodes.

15. A device as claimed in claim 9, 11, 12, 13 or 14 wherein the electrode array further comprises guard electrode elements disposed on both sides of intermediate electrodes in the array; the guard electrodes having dimensions which correspond to those of the individual intermediate electrodes and means for maintaining at least some of the guard electrodes at the same potential as the intermediate electrodes therebetween.

* * * * *